Figure 1:
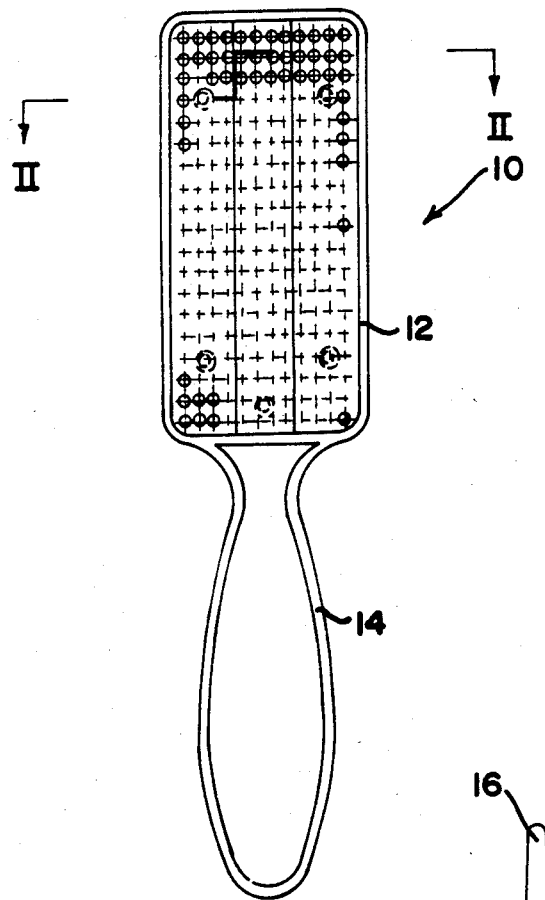

United States Patent [19]

Baker et al.

[11] Patent Number: 4,604,971

[45] Date of Patent: Aug. 12, 1986

[54] INSECTICIDAL GROOMING ARTICLE

[75] Inventors: Rodney C. Baker, Kempton Park; Philippus J. van Rensburg, Randburg, both of South Africa

[73] Assignee: AECI Limited, Johannesburg, South Africa

[21] Appl. No.: 594,531

[22] Filed: Mar. 29, 1984

[30] Foreign Application Priority Data

Apr. 13, 1983 [ZA] South Africa ............ 83/2597

[51] Int. Cl.⁴ .................................... A01K 13/00
[52] U.S. Cl. ............................. 119/86; 119/156
[58] Field of Search ............... 119/86, 83, 93, 156, 119/157; 132/142

[56] References Cited

U.S. PATENT DOCUMENTS

| | | | |
|---|---|---|---|
| 2,238,603 | 4/1941 | Runnels | 132/142 |
| 2,470,024 | 10/1949 | Francis | 119/86 |
| 3,496,589 | 2/1970 | Demner | 15/104.93 |
| 4,143,982 | 3/1979 | Cox et al. | 401/280 |
| 4,150,109 | 4/1979 | Dick et al. | 119/156 |

Primary Examiner—Robert P. Swiatak
Assistant Examiner—Kris R. Schulze
Attorney, Agent, or Firm—Cushman, Darby & Cushman

[57] ABSTRACT

The invention provides an article for grooming an animal and comprising a grooming article of plastics material, the plastics material containing, over at least a portion thereof, at least one insecticide capable of blooming from the article onto the animal when the article is used. The article may be a brush or comb. If desired, only a portion thereof may contain insecticide.

6 Claims, 2 Drawing Figures

U.S. Patent    Aug. 12, 1986    4,604,971

INSECTICIDAL GROOMING ARTICLE

This Invention relates to an insecticidal grooming article.

The present invention provides an article for grooming an animal and comprising a grooming article of moulded plastics material, said plastics material containing, over at least a portion thereof, at least one insecticide capable of blooming from the article onto an animal when the article is used.

The grooming article conveniently is in the shape of a brush or comb. If desired, only some of the bristles of the brush, or teeth of the comb, may contain insecticide, and the remainder may be insecticide-free. In the case of a brush, there may be soft bristles containing the insecticide, and stiff bristles for assisting in the grooming. The different bristles may be in different areas. Alternatively, all the bristles of the brush or teeth of the comb may be of insecticidally-containing plastics material.

If desired, the grooming article may include a replaceable portion containing the insecticide. For example, a middle portion of a brush may be replaceable while the surrounding portions may have bristles which are insecticide-free.

The insecticidal material must be capable of blooming sufficiently to have an insecticidal effect when the article is used to groom an animal, particularly a household animal such as a dog or cat. The insecticide blooms out of the article along the bristles, teeth, or the like, of the brush, comb, or the like.

There may be a single insecticide or a plurality of insecticides. If desired, when there is more than one insecticide, different areas of the grooming article can contain different insecticides. This can overcome or reduce problems of chemical incompatibility of insecticides.

The invention also provides a method of manufacturing a grooming article, which comprises moulding a grooming article from a plastics composition comprising a plastics material and at least one insecticide capable of blooming out of the article, in use.

Conveniently, the composition may also contain a plasticizer as well as other agents which affect the speed with which the insecticide blooms from the article and/or compounds for enabling the insecticide to be retained in the plastics material during moulding. Thus, extenders, fillers, or the like, can be present.

The composition may contain from 10 to 50% (by mass), preferably from 20 to 30% (by mass), plasticizer, and from 5 to 40% (by mass), preferably 10 to 25% (by mass), insecticide.

The insecticide may be any one or more of:
amitraz, (i.e. N,N-di-(2,4-xylyliminomethyl)methylamine);
lindane, (ie 1,2,3,4,5,6-hexachlorocyclohexane);
diazinon, (ie 0,0-diethyl-0-2-isopropyl-6-methylpyrimidin-4-ylphosphorothioate);
dichlorvos, (ie 2,2-dichlorovinyl dimethyl phosphate);
propoxur, (ie 2-isopropoxyphenyl methylcarbamate);
tetrachlorovinphos, (ie 2-chloro-1-(2,4,5-trichlorophenyl)vinyl dimethyl phosphate);
dursban, (ie 0,0-diethyl-0-3,5,6-trichloro-2-pyridyl-phosphorothioate);
carbaryl, (ie 1-naphthalenyl methyl carbamate);
trichlorphon, (ie 2,2,2-trichloro-1-hydroxyethylphosphonate);
phosmet, (ie 0,0-dimethyl S-phthalimidomethylphosphorodithioate) which may be recrystallized to remove or reduce its offensive odour; or a synthetic pyrethroid optionally admixed with a synergist, such as piperonyl butoxide.

Synthetic pyrethroids include:
permethrin (ie 3-phenoxybenzyl-(±)-cis, trans-2,2-dimethyl-3-(2,2-dichlorovinyl)cyclopropane-1-carboxylate);
deltamethrin (ie S-α-cyano-3-phenoxybenzyl-(1R,3R)2,2-dimethyl-3-(2,2-dibromovinyl)cyclopropane-1 carboxylate); and
tetramethrin (ie 3,4,5,6-tetrahydro-phthalimidomethyl(±)cis,trans-chrysanthemate).

The amount of insecticide present may vary, depending on the insecticide, the plastics material, and the other constituents present.

The grooming article provided by the invention can be used for the control of ticks, fleas, or other insects on non-human animals.

Any suitable plastics material may be used. The plastics material may comprise one or more of polyethylene, polypropylene, polyvinylchloride, nylon, nitrile rubbers, ethyl vinyl acetate polymers, and the like. Any suitable method of manufacture may be used, for example injection-moulding.

In addition to the plastics material and the insecticide, plasticisers, extenders, fillers, lubricants, stabilizers, and the like, can be present. The stabilizers may for example be heat stabilizers, such as TBLS, or stabilizers such as calcium oxide, epoxidised soya bean oil, or other suitable epoxy compounds, for one or more of the insecticides. Lubricants can include stearic acid. The plasticiser may, for example, be di-isooctyl adipate. If desired, odour maskers (eg perfumes), or odour absorbers, to overcome unpleasant insecticide smells, may be included.

Examples of extenders are chlorinated hydrocarbons, such as those available under the trade names Cereclor, Conoflex, Mobilsol and Mesamoll, expoxidised soyabean oil, and the like.

Examples of fillers are talc, silica, diatomaceous earth, china clay, and the like.

Although soft plastics materials such as polyethylene and polyvinylchloride can be used, nylon may also be considered. The grooming article must be sufficiently hard to be used without breaking. Since it is normally in the form of a brush or comb, this determines to a large extent the hardness of the plastics material used. It must be flexible but not brittle, and must allow blooming of the insecticide from the article.

If desired, other materials can be used in addition for some of the teeth or bristles, eg steel, animal hair, or the like.

The invention is illustrated in non-limiting manner by reference to the following Examples of compositions which can be used to prepare brushes according to the invention by plastics moulding.

EXAMPLES 1 TO 4

| Constituent | Ex. 1 | Ex. 2 | Ex. 3 | Ex. 4 |
| --- | --- | --- | --- | --- |
| Amitraz | 15,0 | 15,0 | 15,0 | 15,0 |
| Lindane | 15,0 | 15,0 | 15,0 | 15,0 |
| Polyethylene (linear low density) 7042 | 25,0 | 39,5 | 36,5 | 31,5 |
| PVC (Corvic S6611) | 39,5 | 25,0 | 20,0 | 15,0 |
| Heat Stabilizer (TBLS) | 3,0 | 3,0 | 3,0 | 3,0 |

-continued

| Constituent | Ex. 1 | Ex. 2 | Ex. 3 | Ex. 4 |
| --- | --- | --- | --- | --- |
| Calcium oxide stabilizer | 2,5 | 2,5 | 2,5 | 2,5 |
| Nitrile rubber N8 | — | — | 8,0 | 8,0 |
| Stearic acid lubricant | — | — | 0,2 | 0,2 |
| Di-isooctyl adipate plasticizer | — | — | — | 10,0 |

The amounts given above are percentages by weight. The constituents were melted together and the molten mass extruded to form a brush. The brush obtained was suitable for brushing dogs and the like to remove ticks, fleas, etc.

Figure 2:
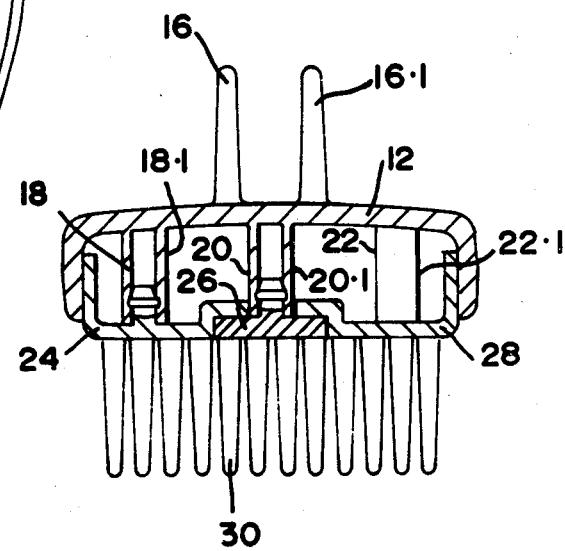

The invention is illustrated by reference to the accompanying drawings, in which FIG. 1 is a plan view of the underside of a brush accordint to the invention; and FIG. 2 is a section along II—II of FIG. 1.

In these Figures, a brush shown generally at 10, has a head 12 and a handle 14.

The head 12 has rows of bristles 16, 16.1 extending from its upper surface and gripping channels 18, 18.1; 20, 20.1 and 22, 22.1 extending from its lower surface. Bristle holders 24, 26, 28 fit in tight frictional grip in the channels 18, 18.1; 20, 20.1 and 22, 22.1.

The central bristle holder 16 has bristles 30 and is moulded from a plastics mixture comprising a plastics material and an insecticide capable of blooming out therefrom.

The outer bristle holders 24 and 28 are also of plastics material but are free from insecticide. The central bristle holder 26 is replaceable.

We claim:

1. An article for grooming an animal which includes a hand-grippable portion and a plurality of teeth or bristles of plastics material attached to the hand-grippable portion, at least some of the teeth or bristles being moulded and flexible and containing, along at least a portion of the teeth or bristles, at least one insecticide, said insecticide being included in said plastics material when said teeth or bristles are moulded therefrom so that the insecticide is moulded therein with the plastics material yet is capable of blooming sufficiently, from the teeth or bristles onto the animal when the animal is groomed with the article, so as to have an insecticidal effect, said plastics material comprising a mouldable polymer and a plasticizer present in sufficient amount to permit effective blooming of the insecticide.

2. An article as claimed in claim 1, wherein the article is in the shape of a comb and all of the teeth of the comb contain the insecticide.

3. An article as claimed in claim 1, wherein the article is in the shape of a brush with only bristles of the plastics material containing the insecticide, so that the insecticide is contained in the bristles along substantially the entire lengths of the bristles.

4. An article as claimed in claim 1, wherein the article is in the shape of a brush which includes, in addition to the bristles of the insecticide-containing plastics material and which contain the insecticide along substantially their entire lengths, also bristles of a non-plastics material.

5. An article as claimed in claim 1, wherein the article is in the shape of a brush, the brush including a replaceable portion having only bristles of the insecticide-containing plastics material and in which the insecticide is contained along substantially their entire lengths, and also including other portions having bristles which are not of insecticide-containing plastics material.

6. An article as claimed in claim 1, wherein the insecticide-containing plastics material comprises from 25–40% (by mass) insecticide.

* * * * *